(12) United States Patent  
Krishnan (10) Patent No.: US 8,834,384 B2  
(45) Date of Patent: Sep. 16, 2014

(54) METHOD AND APPARATUS FOR LOCATING THE FOSSA OVALIS, CREATING A VIRTUAL FOSSA OVALIS AND PERFORMING TRANSSEPTAL PUNCTURE

(75) Inventor: Subramaniam C. Krishnan, Irvine, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1009 days.

(21) Appl. No.: 12/902,897

(22) Filed: Oct. 12, 2010

(65) Prior Publication Data

US 2011/0077507 A1   Mar. 31, 2011

Related U.S. Application Data

(63) Continuation of application No. 11/367,941, filed on Mar. 3, 2006, now Pat. No. 7,815,577.

(60) Provisional application No. 60/658,111, filed on Mar. 3, 2005.

(51) Int. Cl.
| | | |
|---|---|---|
| A61B 5/05 | (2006.01) | |
| A61B 19/00 | (2006.01) | |
| A61B 5/107 | (2006.01) | |
| A61B 5/042 | (2006.01) | |
| A61B 5/06 | (2006.01) | |
| A61B 17/00 | (2006.01) | |
| A61M 25/00 | (2006.01) | |

(52) U.S. Cl.
CPC ............. *A61B 5/042* (2013.01); *A61B 19/5244* (2013.01); *A61B 5/1076* (2013.01); *A61B 19/50* (2013.01); *A61B 2017/00243* (2013.01); *A61B 2019/5251* (2013.01); *A61B 2017/00044* (2013.01); *A61B 5/06* (2013.01); *A61B 2017/00053* (2013.01); *A61M 25/0041* (2013.01); *A61B 2019/505* (2013.01)
USPC ............... 600/508; 600/347; 600/424; 607/1; 607/115; 607/116; 607/118

(58) Field of Classification Search
None
See application file for complete search history.

(56) References Cited

U.S. PATENT DOCUMENTS

| 5,176,140 A | 1/1993 | Kami et al. |
| 5,983,126 A | 11/1999 | Wittkampf |

(Continued)

FOREIGN PATENT DOCUMENTS

EP    1472975    3/2004

OTHER PUBLICATIONS

Bidoggia, Hector "Transseptal Left Heart Catheterization", 1991 pp. 221-225 1991, 221-225.

(Continued)

*Primary Examiner* — Deborah Malamud
(74) *Attorney, Agent, or Firm* — Wiley Rein LLP (57) ABSTRACT

Apparatus is provided of locating the fossa ovalis in a patient by locating at least one of the His bundle, the plane of the interatrial septum, and the coronary sinus ostium in a patient, and thereafter locating the fossa ovalis on the basis of one or more predetermined distances between these locations. Software is also provided that can determine and display the location of the fossa ovalis in a patient based on predetermined distances between the locations. Such software can for example be provided within an electroanatomical system. Methods of determining the location of the fossa ovalis, performed by either a clinician or a central processing unit-controlled surgical system, are also provided and determined using predetermined measurements from defined locations. An apparatus for locating the fossa ovalis and performing a transseptal puncture is also provided.

20 Claims, 9 Drawing Sheets

(56) References Cited

U.S. PATENT DOCUMENTS

| | | |
|---|---|---|
| 6,328,699 B1 | 12/2001 | Eigler et al. |
| 2002/0161422 A1 | 10/2002 | Swanson |
| 2004/0133113 A1 | 7/2004 | Krishnan |
| 2004/0220461 A1 | 11/2004 | Schwartz |
| 2004/0220497 A1 | 11/2004 | Findlay |

OTHER PUBLICATIONS

Gepstein, Lior "A novel method for nonfluoroscopic catheter-based electroanatomical mapping of the heart", *Circulation* 1997;95:1611-1622.

METHOD AND APPARATUS FOR LOCATING THE FOSSA OVALIS, CREATING A VIRTUAL FOSSA OVALIS AND PERFORMING TRANSSEPTAL PUNCTURE

CROSS-REFERENCES TO RELATED APPLICATIONS

This application is a continuation of U.S. application Ser. No. 11/367,941, filed 3 Mar. 2006 (the '941 application), now U.S. Pat. No. 7,815,577, which claims the benefit of U.S. provisional application No. 60/658,111, filed Mar. 3, 2005 (the '111 application). The '941 application and the '111 application are both hereby incorporated by reference as though fully set forth herein.

BACKGROUND OF THE INVENTION a. Field of the Invention

The present invention relates generally to methods and apparatus for locating a patient's fossa ovalis in the atrium of a human heart, creating a virtual fossa ovalis using an electroanatomical mapping system and using the information to perform transseptal punctures. In particular, these methods and apparatus may be based, at least in part, on anatomical measurements.

b. Background Art

Transseptal puncture refers to needle puncture of the interatrial septum through the fossa ovalis and is the standard technique for percutaneous introduction of catheters into the left atrium. The technique was described simultaneously by Ross and Cope in 1959. Brockenbrough and colleagues modified the design of the needle and guiding catheter apparatus in the 1960s. The development of selective coronary angiography in the 1960s led to a refinement of catheterization of the left side of the heart using the retrograde approach. This development, along with the occurrence of complications from the transseptal puncture technique led to a decline in the use of the puncture technique. The development of balloon mitral valvuloplasty as well as catheter ablation of arrhythmias arising from the left atrium (or utilizing left sided bypass tracts) has led to a rapid increase in the use of the technique in recent years.

The goal of the transseptal puncture procedure is to cross from the right atrium to the left atrium through the fossa ovalis. In about 25% of the normal population, the fossa ovalis (the septum primum) has not fused to the rest of the interatrial septum (the septum secundum) and therefore a patent foramen ovale is present. In the rest of the population, access to the left atrium requires a mechanical puncture of this area with a needle and catheter combination.

The danger of the transseptal puncture technique lies in the potential development of complications which can be serious and life-threatening. These include perforation of adjacent structures such as the aorta, the coronary sinus or the free wall of the atrium resulting in cardiac tamponade and death. In the Cooperative Study on Cardiac Catheterization in 1968, 0.2% mortality, 6% major complications, and a 3.4% incidence of serious complications were reported, including 43 perforations. Concern over the potentially grave complications has given the procedure an aura of "danger and intrigue." The complications almost always are due to unintentional puncture of the wrong structure. Therefore, the key to avoiding complications is the correct identification of the fossa ovalis, and accurately directing the needle and catheter through the structure. It is believed that some of the procedure-related complications may be due to insufficient anatomical landmarks and individual variations in the position of the heart with respect to the chest wall.

Transseptal puncture is conventionally performed with X-ray guidance (fluoroscopy). However, fluoroscopy has significant limitations. At best, it provides a shadow of the outer borders of the heart in a single plane and does not identify the intracardiac endocardial structures. Due to the limitations of fluoroscopy and the potential for life threatening complications during transseptal puncture, single plane fluoroscopy alone is not enough. Therefore, more tools have been developed to identify the intracardiac structures. These include: biplane fluoroscopy; use of a pig-tailed catheter to identify the aortic root; pressure manometry to identify aortic/right atrial and left atrial pressures; contrast infusion; and transesophageal (TEE) and intracardiac (ICE) echocardiography.

Biplane fluoroscopy is considered to be expensive and many institutions cannot afford to install such a system in their laboratories. The use of intracardiac (ICE) and transesophageal (TEE) echocardiography to guide the procedure has found increasing popularity in recent years. However, echocardiography also has limitations. The tenting of the fossa ovalis membrane by the transseptal needle visualized by intracardiac echocardiography that one looks for prior to making the puncture may be missed depending on the portion of membrane cut by ultrasound beam. If a different portion of the membrane is tented by the dilator tip, this may not be apparent on the ultrasound picture.

If TEE is used to guide the puncture, a different operator has to operate the TEE system and therefore errors can occur, especially in the interpretation of the data. For example, a different catheter other than the transseptal dilator may be tenting the fossa membrane. In fact, cardiac tamponade and other serious complications can still occur during transseptal puncture, despite the use of ultrasound guidance. In addition, the placement and use of ultrasound catheters requires the insertion of large intravascular sheaths. The additional time and expense of using ultrasound catheters is considerable and routine use of these is impractical.

In summary, the above-described techniques have significant limitations & shortcomings. Thus, there was a need for additional methods and apparatus that assist in identifying the fossa ovalis and which are "user friendly."

Figure 1:
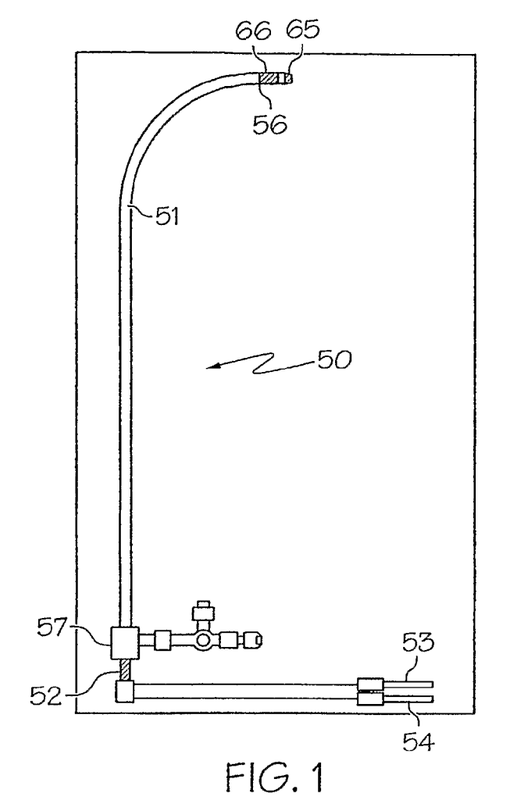
FIG. 1 is a schematic illustration of a transseptal apparatus according to one embodiment of the present invention.

In light of this, Applicant has previously developed apparatus and methods for locating the fossa ovalis and performing transseptal punctures, as described in Applicant's U.S. patent application Ser. No. 10/648,844, filed Aug. 25, 2003 ("the '844 Application," which is incorporated herein by way of reference). The '844 Application describes, among other things, a transseptal apparatus which incorporates electrodes in the dilator tip, as shown in FIG. 1 herein (and FIG. 7 of the '844 Application). In particular, the incorporation of a "tip" and a "ring" electrode into the dilator tip of the transseptal apparatus allows the measurement of electrophysiological properties of the interatrial septum as the dilator tip is dragged down from the superior vena cava. The fossa ovalis may be identified by the presence of low voltage unipolar and bipolar electrograms that are also wider and fractionated as compared to the rest of the interatrial septum. Other identifying properties may include, for example, a lower slew rate, a higher pacing threshold and a lower impedance.

BRIEF SUMMARY OF THE INVENTION

In one embodiment, the present invention provides a method of locating the fossa ovalis in a patient, comprising the steps of:

locating the His bundle, plane of the interatrial septum, and coronary sinus ostium in a patient; and locating the fossa ovalis on the basis of one or more predetermined distances between the fossa ovalis and the His bundle and the coronary sinus ostium.

This method may be performed using an electroanatomical navigation system which includes a display screen configured for displaying the three-dimensional location of one or more catheters positioned within a patient's heart. In general, such systems include one or more processors (e.g., microprocessor or other computing devices), memory for storing executable instructions (e.g., software) for performing the necessary computations and other functions, one or more input devices for receiving user input (e.g., a mouse and/or keyboard), and inputs and outputs in electrical communication with the processor(s). One or more electrode containing catheters, as well as other electrodes, may be operably connected to the system. The catheter(s) are advanced into the patient's heart, and the system senses the electrical activity of the location within the heart where the electrodes provided on the catheter(s) are positioned. At the same time, the system also senses the location of the catheter electrodes or some defined portion of the catheter, in a three-dimensional coordinate system. The thus acquired data may be displayed on the system's display screen—typically in a three-dimensional view which depicts the acquired data points representing structures or surfaces within the heart. The user may manipulate the displayed information in a variety of ways, such as rotating the display of the data in order to provide the desired viewing angle and position, and providing input which identifies certain locations in the heart displayed on the screen (e.g., providing input which designates the location of the coronary sinus ostium, His bundle, etc. based on the displayed data).

In one embodiment, software provided in the navigational system may determine the location of the fossa ovalis, and even display that location (e.g., as a defined area) on the display screen. In this manner, the displayed virtual fossa ovalis can be used as a target for performing a transseptal puncture.

By way of example, the His bundle may be located by positioning an electrode-containing catheter across the tricuspid valve annulus and recording a His bundle electrogram while observing the location of this His catheter on the display screen. If desired, the user may provide input to the system which identifies that the displayed data points representing the three-dimensional locations of the electrodes on the His catheter as defining the location of the His bundle. The plane of the interatrial septum may then be located on the basis of the position of the His bundle catheter, particularly by rotating the displayed data to an LAO view until the tip of the His catheter is "end on" (the tip is displayed on the screen as directly facing the user). Since a His catheter typically has a number of electrodes positioned along its length, the location of these additional electrodes will define interatrial septum. Alternatively, or in addition thereto, the His catheter, as it is advanced towards the His bundle may be used to identify the location of the posteroseptal tricuspid annulus, and its location marked in the navigation system. By connecting points from the His catheter with the location of the posteroseptal tricuspid annulus, the septal plane may be further identified. The coronary sinus ostium may similarly be located by positioning an electrode-containing catheter in the coronary sinus and observing the location of the coronary sinus catheter on the display screen. As is well known to users of these navigational systems, an electrode-containing catheter can be readily observed as it enters the coronary sinus ostium, thereby allowing the user to readily identify the location of the ostium. This location may be identified by the user so that the three-dimensional location of the ostium may be stored in the system.

Once the three-dimensional locations of the His bundle, interatrial septum and coronary sinus ostium have been identified and stored in the system's memory, the navigation system follow executable instructions (e.g., software) in order to determined the approximate location of the fossa ovalis in the three-dimensional coordinate system of the navigational system, using predetermined distances from one or more of the previously located structures. These predetermined distances may be stored in the system's memory, and may include one or more sets of predetermined distances which are used for different patients (e.g., one set for patients with structurally normal hearts and another set for patients with structural heart disease). For example, the location of the fossa ovalis may be determined as an area (e.g., a roughly oval area) lying approximately in the plane of the interatrial septum (e.g., within the plane or up to about 2 mm to the left of the plane of the interatrial septum). The midpoint as well as the anterior and posterior limits of the determined area of the fossa ovalis may be computed using predetermined (and stored) distances from the coronary sinus ostium. The software may also further define the area of the fossa ovalis such that the caudal limit corresponds approximately with the floor of the coronary sinus ostium and/or such that the cranial limit of the defined area is slightly cranial to (e.g., about 2 to about 3 mm) the His bundle. The craniocaudal and transverse dimensions of the defined area may also be determine based on predetermined values stored in the system's memory.

After the navigation system has computed the predicted location of the fossa ovalis in three-dimensional space, electroanatomical navigation system may also be configured to display a visual representation of this location on the display screen. The visual representation may comprise, for example, a "cloud" or other distinct region which may even have general shape of the fossa ovalis. Thereafter, a transseptal puncture may be performed using a transseptal apparatus (either a conventional one or those described further herein the displayed virtual fossa ovalis acts a guide to direct the puncture.

In one embodiment, a transseptal apparatus having one more electrodes at its distal end may be operably connected to the electroanatomical navigation system, such that the location of the distal end (tip) of the transseptal apparatus is displayed on the display screen. In this manner, the user may orient the transseptal apparatus with respect to the displayed virtual fossa ovalis, and thereafter perform a transseptal puncture by directing the distal end of the transseptal apparatus through the fossa ovalis using the displayed visual representation of the location of the fossa ovalis. On the display screen, the user will simply advance the transseptal apparatus so that its distal end, as displayed on the screen, is urged through the virtual fossa ovalis.

The present invention also provides an apparatus for locating the fossa ovalis in a patient, comprising an electroanatomical navigation system having a display screen associated therewith. The system is configured for determining the three-dimensional position of a catheter within a patient's heart and displaying position data representing catheter positions. The electroanatomical navigation system is configured to identify the location of a patient's fossa ovalis on the basis of one or more predetermined distances between the fossa ovalis and the His bundle and the coronary sinus ostium, and to display a visual presentation of the location of the fossa ovalis on the display screen.

The apparatus may further comprise a transseptal apparatus configured for performing a transseptal puncture, the transseptal apparatus including a catheter comprising: a hollow lumen; a first electrode positioned at the distal end of the catheter; and a second electrode positioned on the catheter and spaced proximally from the first electrode, the first and second electrodes operably connected to the electroanatomical navigation system. The catheter may be configured such that the catheter may be inserted into a sheath for a transseptal puncture and a transseptal needle may be urged through the lumen until the tip of the needle protrudes beyond the distal end of the catheter. The catheter is further configured such that the distal end of the catheter can be used as a dilator suitable for penetrating the fossa ovalis during a transseptal puncture procedure by urging the catheter over a transseptal needle positioned within the lumen of the catheter. The distal end of the catheter may be tapered, and the second electrode may be spaced from the first electrode by a distance of between about 2 and about 4 mm.

The embodiments set forth in the drawing are illustrative in nature and are not intended to be limiting of the invention defined by the claims. Moreover, individual features of the drawing and the invention will be more fully apparent and understood in view of the detailed description.

DETAILED DESCRIPTION OF EMBODIMENTS OF THE INVENTION

In the methods and apparatus described in the '844 Application, the fossa ovalis may be identified by changes in electrogram morphology, pacing threshold and/or impedance values. In particular, the fossa ovalis may be located by measuring the electrophysiological ("EP") activity of the fossa ovalis and surrounding heart tissue. By observing differences in the EP activity of tissue at various locations, the operator may determine the location of the fossa ovalis. The lower muscle content and higher fibrous tissue content of the fossa ovalis with respect to the rest of the interatrial septum, as well as the relative "thinning" of the fossa, results in changes in EP activity which may be readily observed via an intracardiac electrogram. For example, the fossa ovalis will record broader, fractionated electrograms of lower amplitude and lower slew rates. Based upon these surprising findings, one or more electrodes for acquiring EP data may be incorporated into a catheter/dilator used during transseptal puncture. As described in the '844 Application, the fossa ovalis may be located on the basis of one or more of the following (wherein the identified change is in relation to the tissue surrounding the fossa ovalis): unipolar voltage reduction; bipolar voltage reduction; signal fractionation; broadened signal; reduced signal slew rate; reduced local myocardial impedance; increased phase angle; and increased pacing threshold. The present invention is a further development of the methods and apparatus described in the '844 Application.

In one embodiment of the present invention, the fossa ovalis is located by identifying the ostium of the coronary sinus ("CS Os") and the plane of the interatrial septum, and thereafter locating the fossa ovalis based on one or more predetermined distances from the CS Os in the plane of the interatrial septum. The fossa ovalis is located as a slight depression in the interatrial septum, and is therefore slightly to the left of the interatrial septum. One or more of the EP properties of the fossa ovalis listed above (and further discussed in the '844 Application) may also be used in conjunction with the predetermined distances in order to confirm that the location of the fossa ovalis has been accurately identified. Once the fossa ovalis has been located, a transseptal puncture may be performed. The puncture may be performed using the transseptal apparatus shown in FIGS. 1 and 2 herein (which correspond to FIGS. 7 and 8 of the '844 Application).

Another embodiment of the present invention provides an apparatus and method for locating the fossa ovalis and creating a virtual fossa ovalis which is displayed to the user, and, if desired, performing a transseptal puncture using the displayed virtual fossa ovalis to guide the puncture. The fossa ovalis is located based on one or more predetermined distances from the CS Os in the plane of the interatrial septum, and optionally one or more of the EP properties of the fossa ovalis discussed above may be used to confirm the location of the fossa ovalis. A display device, such as a display screen associated with an electroanatomical navigation or mapping system, displays a graphical (i.e., visual) representation of the determined location of the fossa ovalis along with one or more other structures within the patient's heart (such as a 3-D representation of the patient's heart). In one embodiment, this "virtual" fossa ovalis may be displayed as a displayed area (e.g., an oval-shaped region displayed on the screen), wherein the dimensions of the displayed area are defined based on predetermined values. The displayed virtual fossa ovalis may then be used to guide transseptal puncture, particular if the location of the tip of the transseptal apparatus (e.g., that shown in FIGS. 1 and 2). is displayed on the same display device, in real time.

Figure 2:
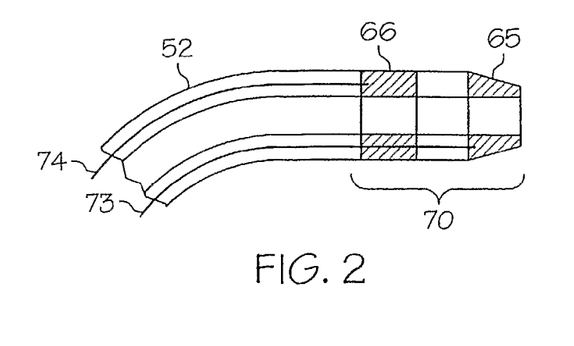
FIG. 2 is a cross-sectional view of the distal portion of the catheter of the transseptal apparatus shown in FIG. 1.

FIGS. 1 and 2 depict a transseptal apparatus 50 according to one embodiment of the present invention which may be used in conjunction with an electroanatomical navigation system to not only locate the fossa ovalis but also to perform a transseptal puncture. Transseptal apparatus 50 is similar to a conventional transseptal apparatus in that it includes a hollow sheath 51 and an internal catheter (sometimes referred to as a dilator) 52. Catheter 52 is hollow and is slightly longer than sheath 51 (typically about 4 cm longer). A guidewire is inserted through the right femoral vein and advanced to the superior vena cava. Catheter (or dilator) 52 is inserted into sheath 51, with the distal end of the catheter protruding beyond the distal end 56 of sheath 51. The sheath and catheter are then advanced over the guidewire into the superior vena cava, and the guidewire is then removed.

Not only is the distal end 70 of catheter 52 tapered, as shown, a pair of electrodes 65 and 66 are provided at the distal end of catheter 52. First, or distal, electrode 65 may be provided at the tip of catheter 52, and second, or proximal, electrode 66 may also be provided at the distal end of catheter 52. In one embodiment, second electrode 66 may be spaced proximally from first electrode 65 by a distance of between about 2 and about 4 mm. The electrodes may, for example, be ring-shaped, with the first electrode measuring between about 2 mm and about 4 mm in length, and the second electrode measuring about 2 mm in length. Electrical leads 73 and 74 are in electrical communication with first and second electrodes 65 and 66, respectively. At the proximal end of catheter 52, electrical leads 73 and 74 are in electrical communication with cables 53 and 54, respectively, which may be attached to an electroanatomical navigation system in the conventional manner (i.e., in the same manner that an EP catheter is operatively connected to such systems).

When connected to an electroanatomical mapping system, catheter 52 and the distal end portion 70 containing electrodes 65 and 66 will perform the same function as a catheter/dilator in a conventional transseptal apparatus. However, catheter 52 differs significantly from a traditional EP catheter in that it has a tapered, rigid distal end and is relatively stiff along its length. The tapered, rigid distal end and stiffness are provided since catheter 52 is specifically designed to perforate the fossa ovalis whereas conventional EP catheters are designed to avoid perforating structures within the patient. The electrodes on the distal end of catheter 52 also allow the catheter to be integrated into the electroanatomical mapping system such that the position of catheter 52 may be visually observed on the display device associated with the navigation system, thereby facilitating proper positioning of the catheter once the fossa ovalis has been located. With some navigation systems, such as the CARTO system (Biosense-Webster Inc. Diamond Bar, Calif.), it may be necessary to include one or more sensors in the distal end of catheter 52 (such as three magnetic field sensors) in order that the location of catheter 52 is displayed on the display device of the navigation system. It is also possible to connect the transseptal needle to the electroanatomical navigation system and visualize this instead of electrodes placed at the tip of the dilator.

Applicant's method for locating the fossa ovalis is described in further detail herein. However, once the operator has confirmed the location of the fossa ovalis and that the distal tip 70 of the catheter 52 is in good contact with the fossa ovalis, a needle may be urged through the central lumen of catheter 52 until the tip of the needle protrudes beyond distal tip 70 through the fossa ovalis and into the left atrium. Thereafter, the catheter 52 may be urged through the fossa ovalis, followed by sheath 51. The catheter 52 and needle are then removed from sheath 51, leaving sheath 51 extending through the fossa ovalis into the left atrium.

Figure 3:
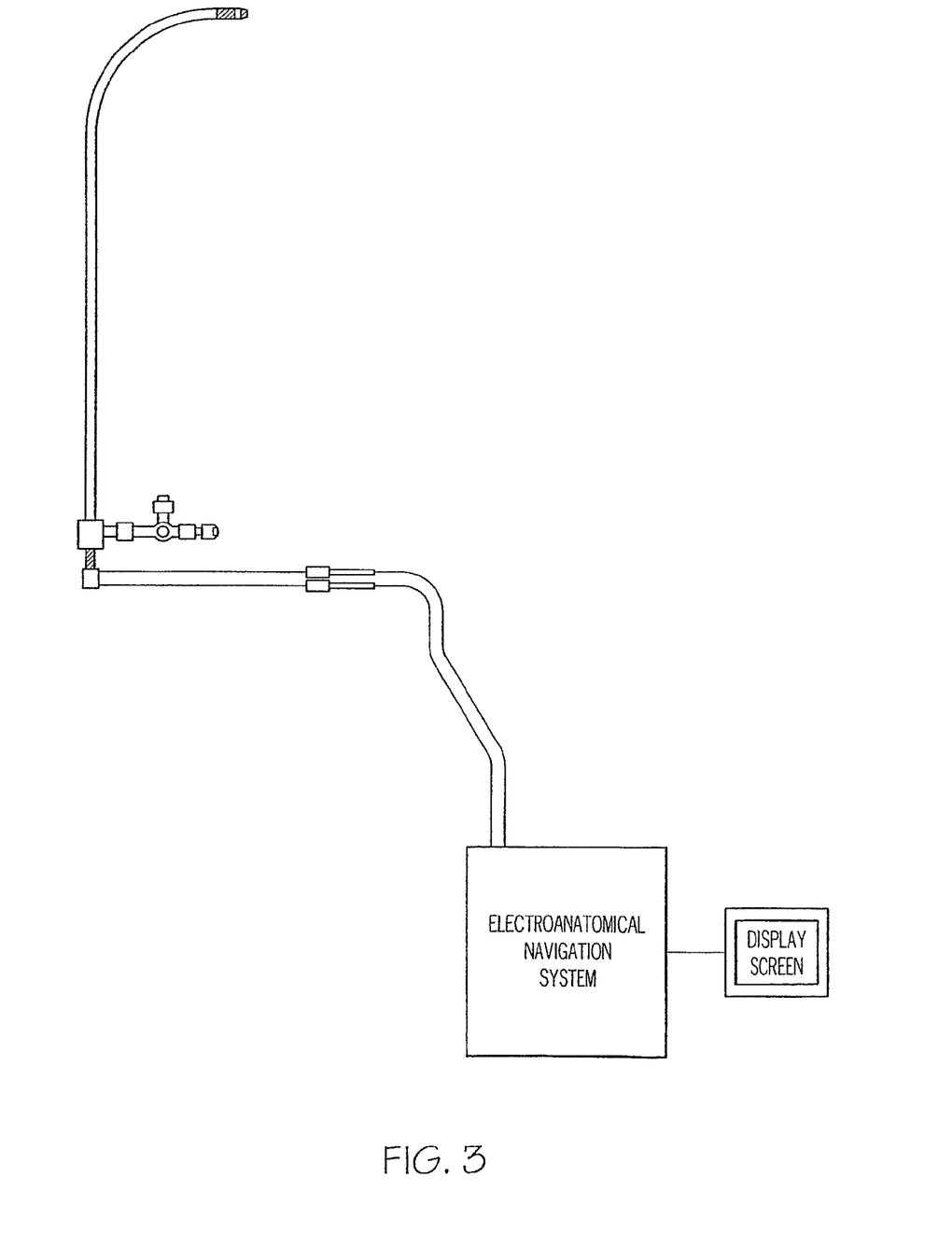
FIG. 3 is a schematic illustration of a system according to the present invention, which includes a transseptal apparatus operatively connected to an electroanatomical navigation system which includes a display screen.

An exemplary apparatus for locating the fossa ovalis and displaying an image of its location with respect to other structures of the patient's heart is shown in FIG. 3 and may include a transseptal apparatus having one or more electrodes in the tip of the dilator (e.g., that shown in FIG. 1), an electroanatomical navigation system and a display screen associated with (or included as part of) the electroanatomical navigation system. The transseptal apparatus is operatively connected with (i.e., in electrical communication with) the electroanatomical navigation system in order to facilitate locating the fossa ovalis and performing a transseptal puncture using the transseptal apparatus. One or more additional catheters, such as those commonly employed in electrophysiology and ablation procedures, may also be operatively connected to the electroanatomical navigation system. These additional catheters may be positioned in the patient's heart in order to further guide the puncture by locating one or more anatomical structures in the heart. In particular, the apparatus may rely on the relationship and known distances between anatomical structures such as the coronary sinus, the His Bundle and the fossa ovalis in order to approximate the location of the fossa ovalis. A virtual fossa ovalis may be determined and displayed on the display screen. In this manner, the physician can use the virtual fossa ovalis as a target during the transseptal puncture.

In another embodiment of the invention, the apparatus may be configured such that the needle of the transseptal apparatus and/or the dilator tip of the transseptal apparatus may be visualized by the electroanatomical navigation system. While FIG. 3 depicts the use of a transseptal apparatus having one or more electrodes in the dilator tip, a conventional transseptal apparatus may be used for puncture, with the location of the fossa ovalis determined using one or more conventional catheters used with electroanatomical navigation systems.

During cardiac ablation procedures, electrode-containing catheters are typically positioned at specific regions of the heart which define distinct anatomical landmarks, particularly the His bundle, and/or the coronary sinus. These catheters assist with the identification of the aortic root, the ostium of the coronary sinus, the plane of the interatrial septum and other critical structures. In the present invention, these electrode-containing catheters may also be used to define anatomical landmarks to guide the transseptal apparatus and needle provided therein to the fossa ovalis in conjunction with an electroanatomical navigation system.

Figure 4:
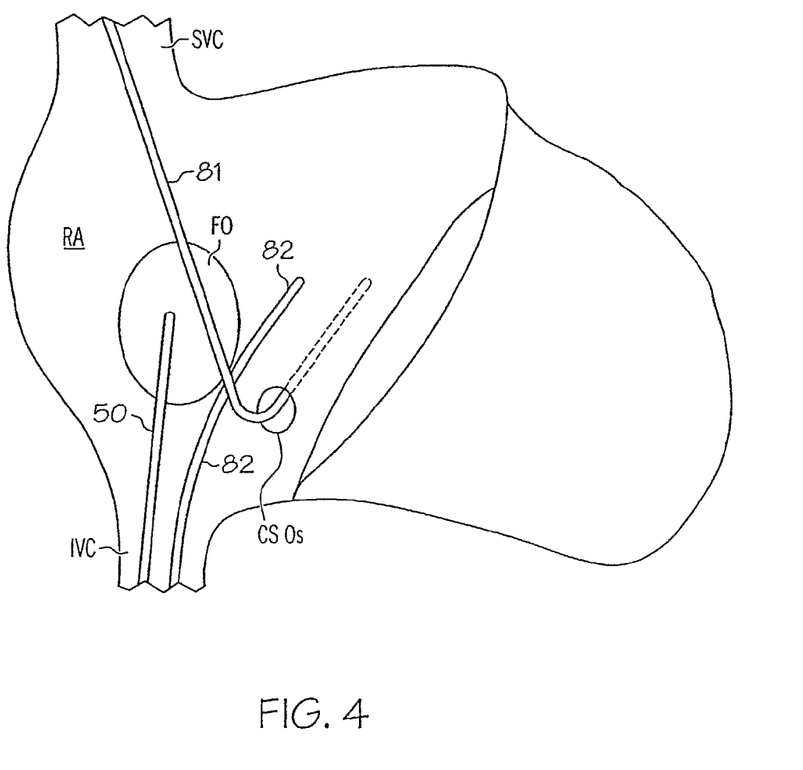
FIG. 4 is an RAO view of a heart along with a His catheter, a catheter extending through the coronary sinus, and a transseptal apparatus.

FIG. 4 is a right anterior oblique ("RAO") view of a patient's heart, with a catheter 81 inserted through the superior vena cava (SVC), into the right atrium (RA) and into the coronary sinus through the CS Os. Another catheter 82 extends through the inferior vena cava (IVC), and is positioned across the tricuspid valve annulus to record a His bundle electrogram. These catheters are routinely placed in the heart during electrophysiology procedures, and can be imaged using, for example, fluoroscopy or an electroanatomical navigation system. FIG. 4 also shows a transseptal puncture apparatus 50 which has been inserted through the inferior vena cava into the right atrium, wherein the tip of the apparatus is in contact with the fossa ovalis (identified at FO). In the RAO view of FIG. 4, the fossa ovalis is posterior to (i.e., to the left of) the coronary sinus ostium. In the RAO fluoroscopic view where the interatrial septum is seen best, the posterior structures will be to the left on the display screen and the anterior structures will be to the right on the display screen.

As further described herein, the catheters shown in FIG. 4 and certain relations of anatomical structures of the heart, such as the distance from the coronary sinus ostium to the fossa ovalis, are used to guide the transseptal puncture. Applicant has discovered a relationship of the coronary sinus and the aortic root (as identified by a catheter recording His bundle electrograms) to the fossa ovalis. In addition, the His bundle catheter (along with or without identifying the posteroseptal tricuspid annulus) can be used to identify the plane of the interatrial septum, and the fossa ovalis is located on this plane. This information can be used to help locate the fossa ovalis and guide transseptal puncture. In addition, this information can be used in conjunction with changes in electrogram morphology, pacing threshold and/or impedance values acquired in the manner described in the '844 Application. in order to further locate the fossa ovalis.

Figure 5:
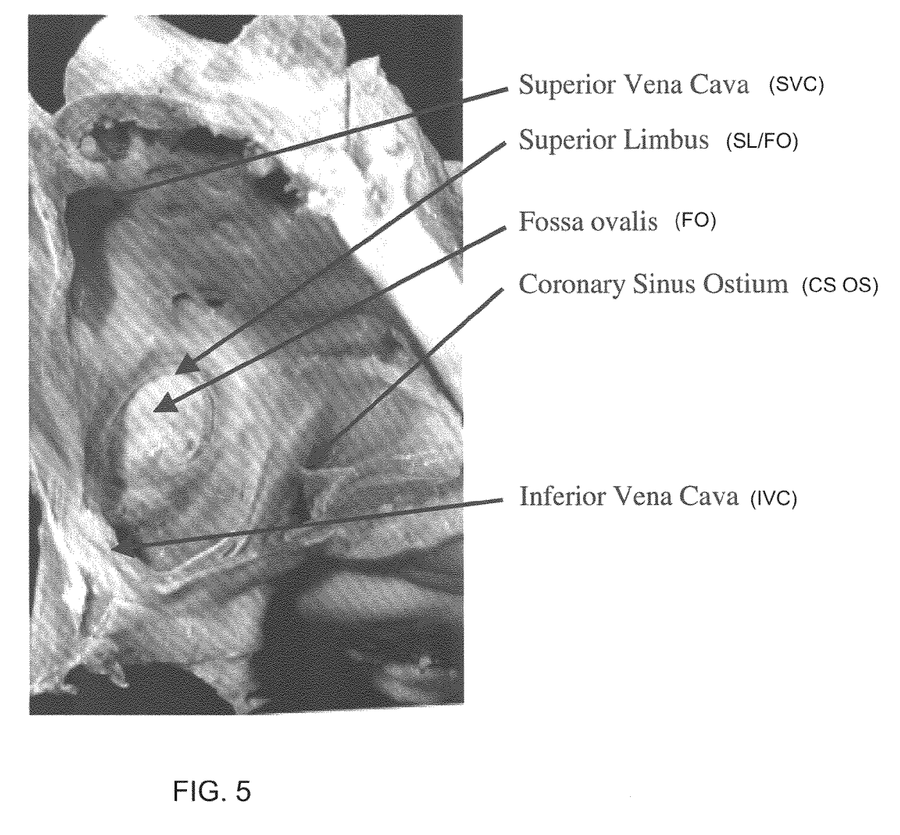
FIG. 5 is an RAO view of a heart wherein the lateral wall of the atrium has been removed.

FIG. 5 is an RAO view of a heart wherein the lateral wall of the atrium has been removed, the fossa ovalis (FO) is a thin fibromuscular partition which is posterior to the coronary sinus ostium (CS Os). Applicant has determined that the superior or cranial limit of the fossa ovalis (superior limbus "SL/FO" in FIG. 5) is about 2-3 mm superior to the location of the His bundle. As discussed in the '844 Application, unlike the rest of the interatrial septum, the fossa ovalis is largely a fibrous structure (comprising about 70% fibrous tissue and 30% muscle).

The coronary sinus (CS) is a tubular structure just above the posterior left atrioventricular junction and is of special interest to the electrophysiologist. It opens into the right atrium between the inferior vena cava (IVC in FIG. 5) and the tricuspid valve orifice. Its tributaries are the great, small and middle cardiac veins, the posterior vein of the left ventricle and the oblique vein of the left atrium. Left atrial recording for electrophysiology (EP) studies is routinely done indirectly from the coronary sinus. The CS can be cannulated from the jugular, subclavian or femoral vein fairly easily. Because of its role in providing information about left atrial activation during various arrhythmias, it is routinely cannulated with electrode catheters during electrophysiology and ablation procedures.

The aortic root is adjoining the anterosuperior portion of the tricuspid annulus & septum. Perforation of the aorta is a potential complication of a transseptal puncture procedure. In the EP lab, the His bundle catheter is normally placed across the tricuspid valve and is used to identify the noncoronary cusp of the aortic valve. As mentioned previously, the His bundle catheter also provides a rough approximation of the superior limbus of the fossa ovalis i.e. the superior margin above which the puncture should not be made. In particular, Application has found that the superior limbus is approximately 2-3 mm superior (above, in the RAO view of FIG. 4) to the location of the His bundle (the tip of catheter 82 in FIG. 4).

The His bundle catheter can also be used to identify the plane of the interatrial septum. This is best seen in the left anterior oblique (LAO) view of FIG. 6 wherein the His bundle catheter 82 is "end on" (i.e., the tip of the His catheter, identified at HB, is visible, while in the RAO view only the side of the His catheter is visible). This can also be seen quite well using fluoroscopy. In other words, in the LAO view of FIG. 6, the side of the His catheter is positioned against the interatrial septum.

Figure 6:
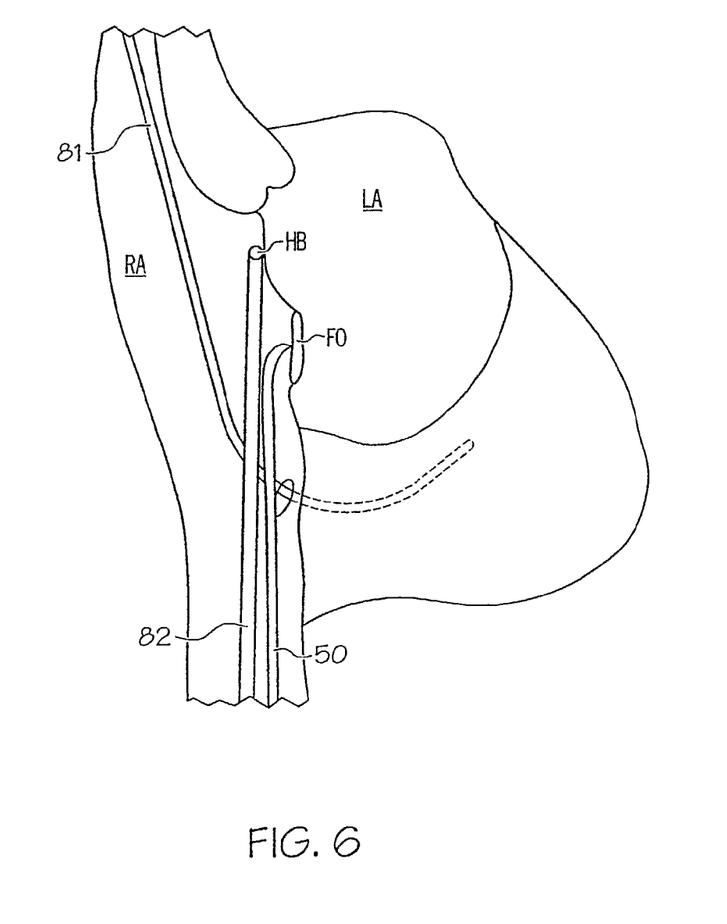
FIG. 6 is an LAO view corresponding to FIG. 4.

As shown in FIG. 6, the tip of the transseptal apparatus 5o when it indents the fossa ovalis is to the left of the septal plane, which is to the viewer's right in the LAO view of FIG. 6. This feature is also used by many operators during the procedure, as described, for example, in PCT Publication No. WO02/058780, which is incorporated herein by way of reference. In FIG. 6, the site of puncture (fossa ovalis, or FO) is to the left of the septal plane as defined by the His bundle catheter (in the LAO view).

Applicant has discovered that the fossa ovalis can be located based on predetermined distances from other structures in the heart. Since these other structures can be readily located using catheters that are routinely placed in the heart for electrophysiology and ablation procedures, the location of the fossa ovalis can also be readily determined using these predetermined distances. The predetermined distances of the fossa ovalis from other structures in the heart may be determined, for example, by measurements of a plurality of exemplary hearts. In order to improve the accuracy and applicability of the predetermined distances used in the methods and apparatus of the present invention, measurements may be made on a large number of hearts from individuals of various demographics (e.g., age, size, sex, etc.) and having various medical conditions (particularly various forms of organic heart disease). In addition, previous imaging studies or angiography on a particular patient may provide very precise measurements of the predetermined distances appropriate for that particular patient in a subsequent transseptal puncture or other procedure requiring location of the fossa ovalis.

Figure 7:
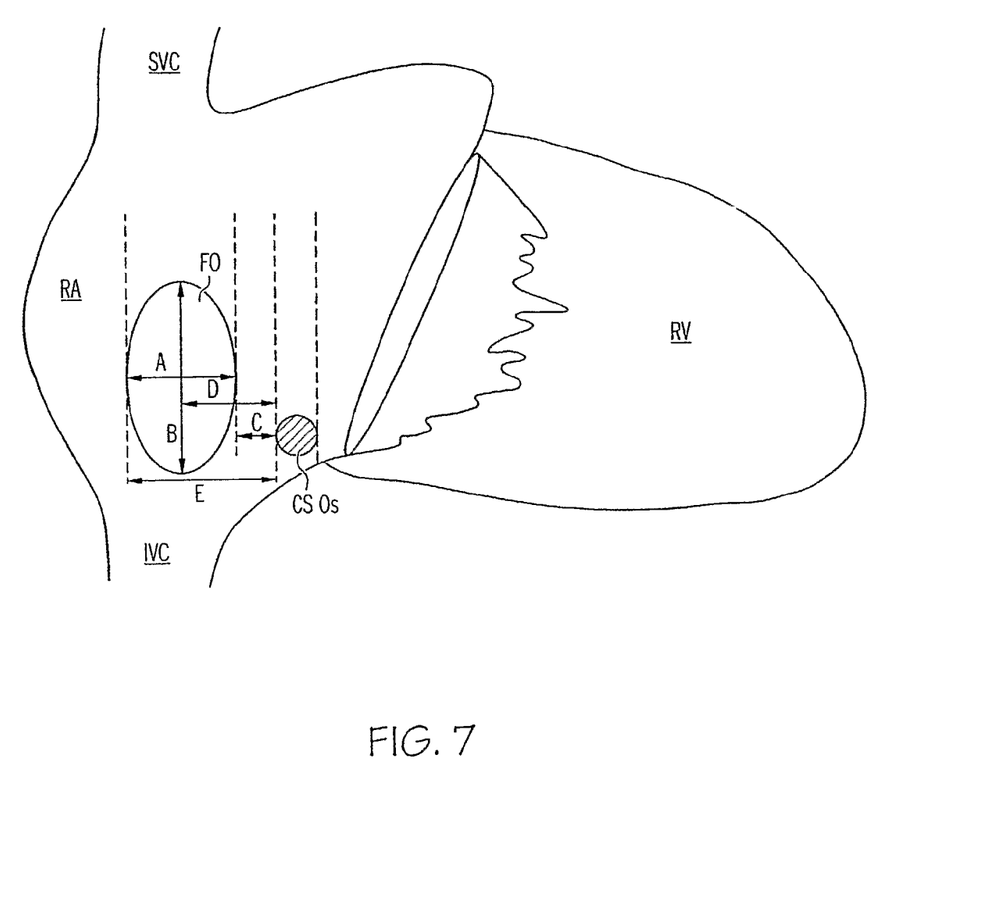
FIG. 7 is a schematic illustration depicting predetermined distances from the coronary sinus ostium to the fossa ovalis.

In order to determine the relationships between anatomical landmarks and structures in the interatrial septum, Applicant made measurements in autopsied hearts. Seventy two hearts from the Jesse Edwards Registry (St. Paul, Minn.) were examined: 18 were structurally normal; and 54 had organic heart disease (OHD). The OHD was of the following types: atherosclerotic coronary artery disease (17%), atherosclerotic coronary heart disease (25%), ventricular hypertrophy (51%), dilated cardiomyopathy (21%), cardiac enlargement (26%), rheumatic heart disease (6%), infective endocarditis (3%), and nonrheumatic valvular heart disease (15%). The measurements which were made focused on the dimensions of the fossa ovalis and the distance between this structure and the coronary sinus ostium. The distances which were measured are depicted in FIG. 7, wherein:

A=transverse dimension of the fossa ovalis
B=craniocaudal dimension of the fossa ovalis
C=distance from the posterior lip of the coronary sinus ostium to the anterior limbus of the fossa ovalis
D=distance from the posterior lip of the coronary sinus ostium to the midpoint of the fossa ovalis
E=distance from the posterior lip of the coronary sinus ostium to the posterior limbus of the fossa ovalis Because the fossa ovalis is typically approximates an oval shape, measurements C-D are taken from vertical tangents as shown in FIG. 7.

Applicant's measurements are reported in the table below (in millimeters).

|  | All N = 72 | Normal N = 18 | Abnormal N = 54 |
| --- | --- | --- | --- |
| Transverse FO (A) | 18.74 ± 6.69 | 16.67 ± 4.42 | 19.44 ± 7.19 |
| Craniocaudal FO (B) | 20.06 ± 7.39 | 17.42 ± 3.46 | 20.94 ± 8.13 |
| Posterior lip of CS Os To anterior limbus (C) | 11.50 ± 3.84 | 9.97 ± 6.34 | 12.01 ± 3.86 |
| Posterior lip of CS Os To mid-point of FO (D) | 20.55 ± 5.80 | 17.44 ± 2.86 | 21.58 ± 6.17 |
| Posterior lip of CS Os To posterior limbus (E) | 29.29 ± 8.97 | 25.03 ± 3.68 | 30.71 ± 9.76 |

It should be noted that the above measurements are based on a relatively small subset of hearts, and therefore additional data may lead to other values which differ from those indicated above. For example, additional measurements may provide other, more appropriate predetermined distances for individuals of varying ages, sex and medical conditions. Therefore, the present invention is not limited to the use of the predetermined distances reported in the table above.

The above data may be used to locate the fossa ovalis in a patient by identifying the location of the coronary sinus ostium, and simply measuring distances from the posterior lip of the CS Os in the plane of the interatrial septum. The location of the caudal limit of the fossa ovalis may also be approximated as corresponding to the floor of the coronary sinus ostium, and the location of the cranial limit of the fossa ovalis approximately 2-3 mm cranial to the tip of the His bundle catheter. With this information, the location of the fossa ovalis can be precisely predicted.

In particular, the predetermined distances described above may be used in connection with, or even incorporated into, various electroanatomical navigation systems commonly available to practitioners. When incorporated into such systems, this data may even be used to create a virtual fossa ovalis—i.e., a visually-identified zone which corresponds to a three-dimensional region in the heart where the fossa ovalis is likely to be present. This virtual fossa ovalis may be depicted on a display device associated with an electroanatomical navigation system in any of a variety of manners which facilitates transseptal puncture using the virtual fossa ovalis to guide the puncture. In addition, the predetermined measurements may be used in conjunction with one or more of the electrophysiological parameters of the fossa ovalis (particularly as compared to the surrounding tissue, as described in the '844 Application) in order to more accurately predict the location of the fossa ovalis.

Any of the various electroanatomical navigation systems known to those skilled in the art may be used in order to guide transseptal puncture a) by visualizing the dilator tip that has electrodes b) identifying the septal plane by the His catheter c) calculating a fixed distance posterior to the ostium of the coronary sinus in the RAO view and creating a "virtual" fossa ovalis on the display screen associated with the navigation system.

One particular type of navigation system is known as the LOCALISA (formerly available from Medtronic) or the ENSITE system operating with NAVX software and components (formerly available from Endocardial Solutions, now available from St. Jude Medical, Inc.) intracardiac navigation systems. Named after the term "localization," the LOCALISA system was the first to provide three-dimensional visualization of conventional EP catheters during EP studies and ablation procedures. The basic operating principles of the ENSITE system are described in further detail in U.S. Pat. Nos. 5,983,126 and 6,955,674, both of which are incorporated herein by way of reference.

The ENSITE system allows real-time imaging of catheters and the marking of intracardiac points of interest by the user (e.g., using an input device such as a computer mouse associated with the system). This mapping system also provides real-time, nonfluoroscopic, 3-D navigation without requiring a special mapping catheter. It does this by recording the voltage potentials on regular electrodes within three electric fields that define a coordinate system. These potentials are translated into a measure of distance in relation to a fixed reference catheter, giving the operator a 3-D representation of catheter locations within the heart chamber. Individual locations can be saved, annotated, and revisited later. Tests show that catheters can be returned to within 2 mm of a previously marked position with 99% confidence. The system is also sufficiently accurate for detailed catheter mapping and the creation of linear or complex RF lesion patterns. A more advanced version of this system is the ENSITE system operating with NAVX software and components (formerly known as Endocardial Solutions, now St. Jude Medical, Inc.) which uses LOCALISA technology but with more advanced software that allows visualization of a greater number of electrodes.

Another electroanatomical navigation system commonly employed is the CARTO Electroanatomical Mapping & Navigation System (Biosense-Webster Inc. Diamond Bar, Calif.). The CARTO system is yet another nonfluoroscopic electroanatomical mapping and navigation system. The catheters used in this system have miniature magnetic field sensors and a location pad positioned beneath the patient emits an ultralow magnetic field. The system provides simultaneous electrophysiological and spatial information. It also allows for 3-D reconstruction of cardiac chambers. The CARTO system is further described in U.S. Pat. Nos. 5,391,199 and 6,301,496, as well as U.S. Patent Pub. Nos. 2002/0165448 and 2004/0039293, all of which are incorporated herein by way of reference.

Yet another electroanatomical navigation system is the Cardiac RPM system (from Boston Scientific Corp.). This system uses ultrasound ranging to triangulate catheter positions inside a beating heart.

The methods of locating the fossa ovalis using an electroanatomical navigation system will be described in connection with the ENSITE system. However, it will be understood that the present invention is not limited to the use of such systems, as the methods described herein can be used with any electroanatomical navigation system.

The Right Anterior Oblique (RAO) & Left Anterior Oblique (LAO) projections are selected based on the orientation of the septum determined by the direction of the electrode catheter recording the His bundle electrogram (the tip of the His catheter should be end on in the LAO view). Since the septal plane will vary slightly in different individuals, the LAO projection where the His bundle catheter is "end on" will also be different. The RAO view angle is set perpendicular to the LAO plane (and this view will also be different for individual patients). This view should allow visualization of the entire interatrial septum. In addition, it is also contemplated that the location of the posteroseptal tricuspid annulus may be marked three-dimensionally and this location used, along with locations in the anteroseptal tricuspid annulus (obtained via the His Bundle catheter), to establish the septal plane.

Figure 8:
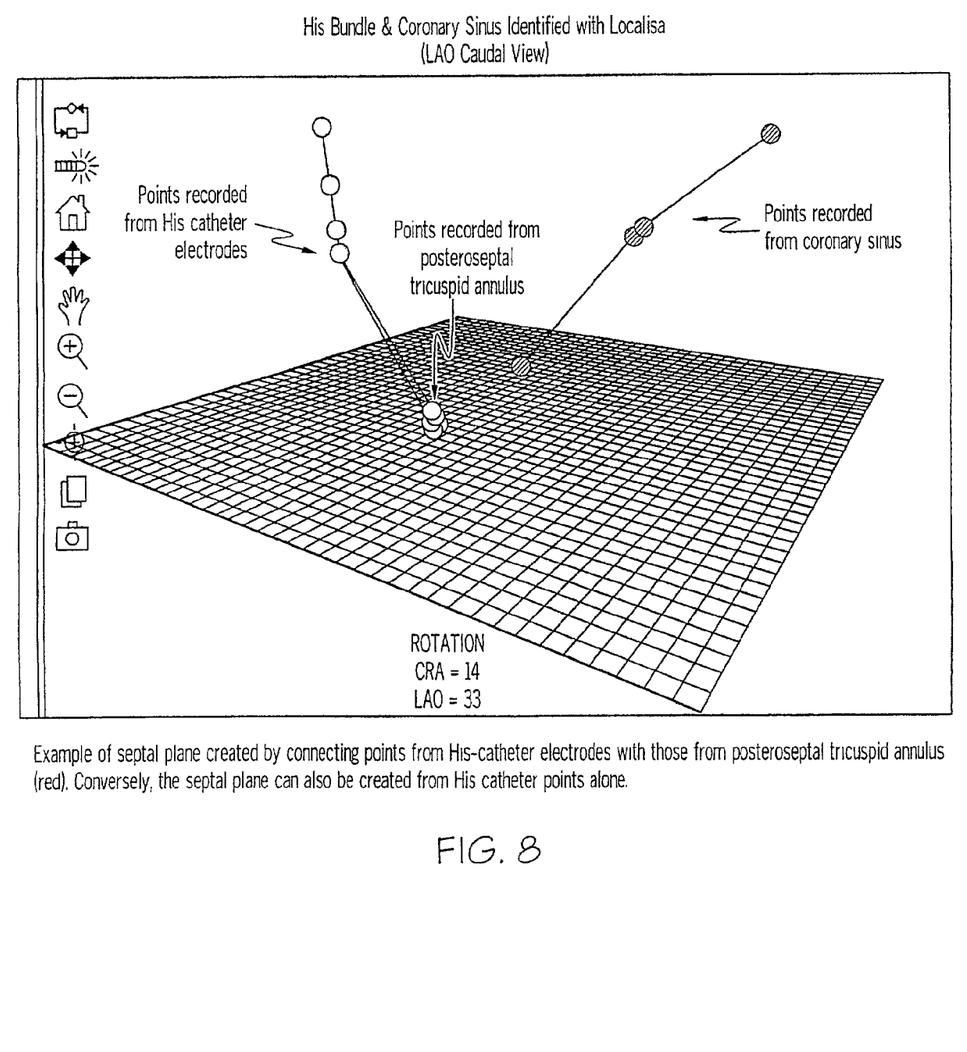
FIG. 8 is an LAO screen shot from an electroanatomical system.

As is well known to those skilled in the art, catheters operatively connected to a standard system for electroanatomical mapping (e.g., a ENSITE system) are placed in the coronary sinus, and across the anteroseptal tricuspid annulus to record a His bundle electrogram. As seen in the LAO view of FIG. 8 displayed by a ENSITE system, the electrodes on the His catheter are visually displayed. A His catheter typically has multiple electrodes along its length, and therefore the series of points representing the electrodes along the length of the His catheter can be used to identify the septal plane. Alternatively, or in addition thereto, the posteroseptal tricuspid annulus may be identified, such as by using the His catheter, and its location marked in the navigation system. By connecting points from the His catheter with the location of the posteroseptal tricuspid annulus, the septal plane may be identified. As is known to those skilled in the art, once an anatomical structure has been identified by the user, its location may be marked in the navigation system based on user input. For example, once a particular structure or location has been identified, the user may provide an input to the system (e.g., a mouse click) at the point which the user desires to mark, in combination with a user input which tells the system what the selected point represents (e.g., mouse click on one or more points along with a user input which identifies those points as representing the location of the posteroseptal tricuspid annulus). In this manner, the same catheter may be used to locate and mark the posteroseptal tricuspid annulus as well as the His bundle. The coronary sinus catheter electrode positions may similarly be used to identify not only the location of the coronary sinus ostium, but also the plane of the mitral annulus.

Figure 9:
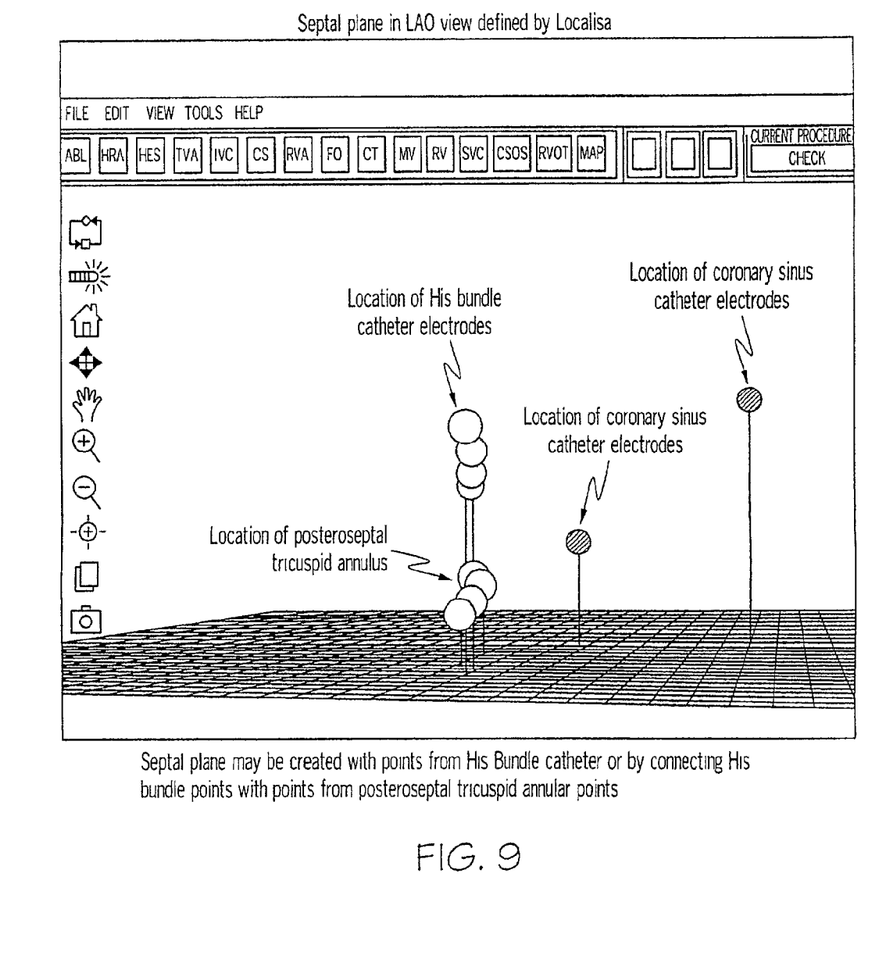
FIG. 9 is an LAO screen shot from an electroanatomical system.

Once the septal plane has been identified, the user may rotate the LAO view in the conventional manner until the His catheter is positioned "end on," as shown in FIG. 9. In other words, the points representing the electrodes along the length of the His catheter will be vertically aligned with one another, as shown. By orienting the LAO view in the manner shown in FIG. 9, the optimal RAO view angle for viewing the entire interatrial septum may be set perpendicular to the LAO view angle of FIG. 9. This optimal RAO view angle will further facilitate display of the virtual fossa ovalis and assist in guiding transseptal puncture.

Once the septal plane and coronary sinus ostium have been identified and their locations marked in the navigational system, the location of the fossa ovalis may be determined based on the predetermined distances discussed previously. For example, the user may rotate to an RAO view which is perpendicular to the angle of the LAO view of FIG. 9. Thereafter, the user may simply measure the appropriate distances from the CS Os and the His bundle in order to identify the location of the FO, and thereafter perform the transseptal puncture using, for example, the apparatus shown in FIG. 1. Since this transseptal apparatus includes electrodes operatively connected to the navigation system, its location will even be displayed on the display screen in relation to the OS Cs and His bundle.

In order to further simplify locating the fossa ovalis, the navigation system itself may be configured to compute the location of the FO and display that location to the user, particular in an RAO view perpendicular to the LAO view of FIG. 9. The location may be displayed as a "virtual" fossa ovalis in (or slightly to the left of) the septal plane. In one embodiment, the predetermined distances used by the software to create the virtual fossa ovalis may include one or more of the following: a) the cranial limit of the fossa ovalis is about 2 to 3 mm cranial to the His bundle catheter; b) the caudal limit of the fossa ovalis is approximately the floor of the coronary sinus ostium; c) the virtual fossa ovalis is created slightly to the left (about 2 mm) of the plane of the interatrial septum; d) the anterior limit of the virtual fossa ovalis (in the RAO view-90 degrees perpendicular to the plane of the interatrial septum), representing the anterior limbus, is about 12 mm from the coronary sinus ostium; e) the posterior limit of the virtual fossa ovalis representing the posterior limbus is about 30 mm from the coronary sinus ostium; f) the midpoint of the fossa ovalis is approximately 20 mm from the coronary sinus ostium; g) the craniocaudal dimensions of the virtual fossa ovalis will be approximately 18 mm; and h) the transverse dimension of the virtual fossa ovalis will be approximately 20 mm.

The above distances are based on measurements of hearts, as reported herein, and includes both normal and abnormal hearts. For normal hearts, the predetermined distances (d)-(g) may be: (d) about 6 to about 13 mm; (e) about 21 to about 29 mm; (f) about. 14 to about 20 mm; (g) about 14 to about 21 mm; and (h) about 12 to about 21 mm. For abnormal hearts, particularly those with organic heart disease, the predetermined distances (d)-(g) may be: (d) about 8 to about 16 mm; (e) about 21 to about 40 mm; (f) about 15 to about 28 mm; (g) about 13 to about 29 mm; and (h) about 12 to about 27 mm. Of course these predetermined distances are merely exemplary.

Thus, once the locations of the coronary sinus ostium and His bundle, as well as the plane of the interatrial septum have been determined and designated in the navigation system, the software in the system may easily determine the location of the fossa ovalis based upon the predetermined distances described herein. As shown in the RAO view of FIG. 10 which is perpendicular to the LAO view of FIG. 9, the location of the fossa ovalis may be displayed as a defined region on the display screen such as in the form of a cloud or other visible indicia. This virtual fossa ovalis is then used as a target for guiding transseptal puncture.

It is anticipated that in some patients, particularly those with structural heart disease, it may be more difficult to define the anterior and posterior limits of the fossa ovalis in a precise manner Even in patients without structural heart disease, the location of the fossa ovalis will vary somewhat from one patient to another. In one embodiment of the present invention, this reduced precision may also be visually indicated on the display screen. For example, in the case of a virtual fossa ovalis in the form of a cloud, the density of dots in the cloud may be reduced, particularly in cases in which the patient is known to have structural heart disease (the user may simply indicate this fact to the navigational system) The higher density of dots will represent a higher probability of locating the fossa ovalis. The system may also be configured to display a higher density of dots nearer the center of the predicted location of the FO. Of course the reduced precision may be displayed in a variety of other ways, such as displaying the virtual fossa ovalis in different colors depending on the expected level or precision (e.g., green=higher precision, yellow=less precision, red=even less precision).

Software in the electroanatomical navigation system may identify the location of the fossa ovalis in accordance with the methods described herein. For example, the software may be configured to locate the coronary sinus, the septal plane and the His bundle based on data indicative of the position of catheters positioned within the coronary sinus ostium and at the His bundle. The software may be further configured to utilize this data in conjunction with stored information regarding the relationship and known distances between the fossa ovalis and the coronary sinus and His Bundle in order to approximate the location of the fossa ovalis. The computed location of the fossa ovalis may be depicted on the display screen associated with the electroanatomical navigation system, particularly in relation to the position of the transseptal apparatus and the other catheters positioned within the heart. The location of the fossa ovalis may be depicted on the display screen as a "virtual fossa ovalis." In this manner, the physician can use the virtual fossa ovalis as a target during the transseptal puncture.

Figure 10:
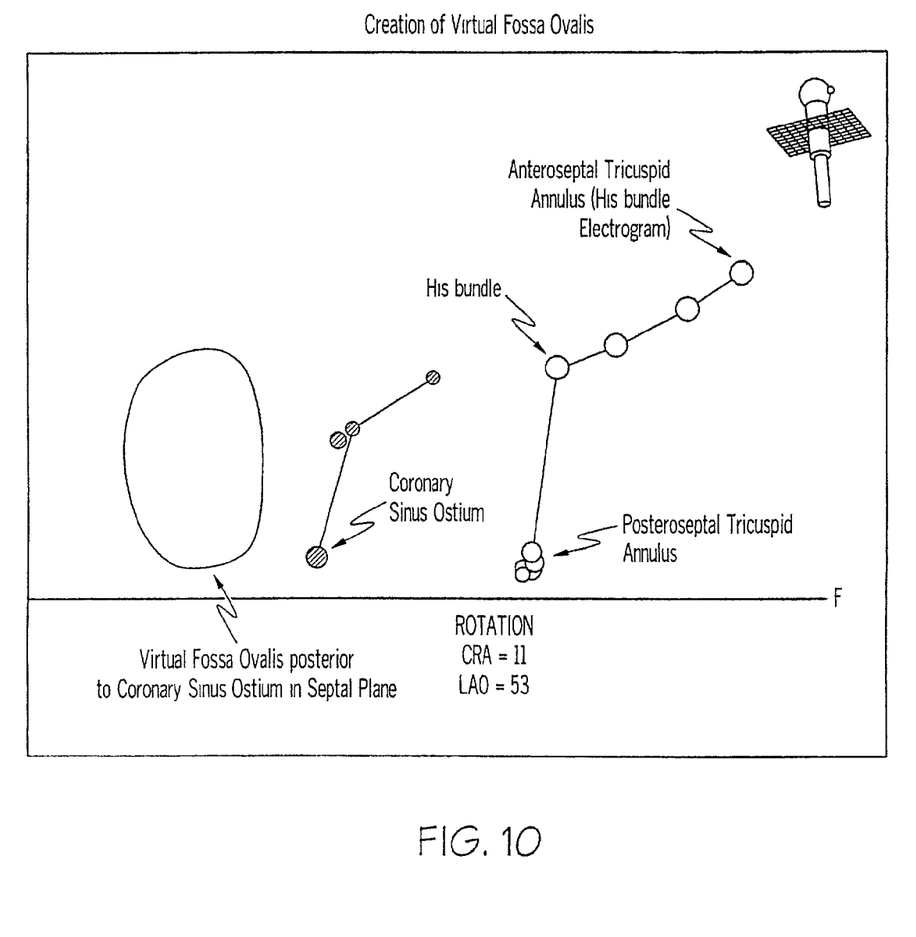
FIG. 10 is an RAO screen shot from a system according to the present invention.

Once the location of the fossa ovalis has been determined and displayed on the screen, the orientation of the transseptal puncture apparatus prior to puncture may be adjusted so that it is: (a) approximately perpendicular to the septal plane (as recorded by the His catheter); and (b) approximately parallel to the plane of the mitral annulus (as recorded by the coronary sinus catheter). Since the transseptal apparatus includes electrodes in its distal end, its location will be displayed on the screen along with the location of the fossa ovalis and other identified structures and locations. The virtual fossa ovalis will represent the intended site of puncture, and, in FIG. 10 is depicted as a "cloud" in (or slightly left of) the septal plane. Of course this is merely exemplary, since any visible indicia may be displayed as the virtual fossa ovalis. Transseptal puncture may then be performed in the usual manner (i.e. directing the needle of the transseptal apparatus and catheter through the virtual fossa ovalis.

While in the case of LOCALISA or ENSITE, the catheter electrode positions can be recorded from the catheters themselves, with the CARTO system, it may be necessary for the mapping catheter to be placed in the region of the His Bundle, the coronary sinus and record data. The electrode positions recorded represent anatomical structures (the currently available CARTO system does not allow for multiple catheters to be visualized simultaneously). In fact, regardless of which navigation system is used, it is not necessary to keep all of the EP catheters in place during the procedure. For example, a single mapping catheter may be used to identify the CS Os, the His bundle and the septal plane—once identified, these structures may simply be recorded in the system and even displayed on the screen when the catheters are no longer in place. Such a single catheter may comprise, for example, a deflectable catheter which may be deflected or straightened, as needed (e.g., using pullwire technology) in order to direct the catheter to the structures to be located.

The specific illustrations and embodiments described herein are exemplary only in nature and are not intended to be limiting of the invention defined by the claims. For example, the present invention is not limited to the specific commercially-available electroanatomical navigation systems discussed and described herein. Rather, the present invention encompasses the use of any electroanatomical navigation system which is capable of locating electrodes and/or catheters in a three-dimensional space, include systems hereafter developed. Further embodiments and examples will be apparent to one of ordinary skill in the art in view of this specification and are within the scope of the claimed invention.

What is claimed is:

1. An apparatus for locating the fossa ovalis in a patient, comprising:
   an electroanatomical navigation system, said electroanatomical navigation system configured for determining the position of at least one catheter within a patient's heart; wherein
   said electroanatomical navigation system is configured to identify the location of a patient's fossa ovalis on the basis of one or more predetermined distances measured from one or more of the His bundle, the coronary ostium, and the plane of the interatrial septum; and
   means for displaying the position of the fossa ovalis and the at least one catheter on a display screen.

2. An apparatus according to claim 1, wherein the means for displaying the fossa ovalis comprises an indication of a probability for locating the fossa ovalis at at least one point.

3. An apparatus according to claim 2, wherein the indication comprises at least one of: a density of dots, a color, a flashing icon, a clarity of display, and a brightness of the visual indication.

4. An apparatus according to claim 3, wherein at least one of an audible indication, a tactile indication, and a visual indication is triggered due to a position of the at least one catheter in relation to the fossa ovalis.

5. An apparatus according to claim 1, wherein the electroanatomical navigation system has at least one of: an impedance-measuring electrode element, a magnetic field sensor element, an acoustic-ranging system element, a computed tomography element, and a magnetic resonance imaging element.

6. A non-transitory computer-readable medium comprising instructions to cause a processor to locate the fossa ovalis on the basis of one or more of the location of the plane of the patient's fossa ovalis, the location of the patient's His bundle, and the location of the patient's coronary sinus ostium.

7. A non-transitory computer-readable medium according to claim 6, further comprising instructions to display the location of the fossa ovalis on a graphical user interface.

8. A non-transitory computer-readable medium according to claim 7, wherein the display includes a visual indication of a probability for locating the fossa ovalis at the then present displayed location.

9. A non-transitory computer readable-medium according to claim 8, wherein the processor displays the probability as at least one of: a density of dots, a color, a flashing icon, a clarity of the visual indication, and a brightness of the visual indication.

10. A non-transitory computer-readable medium according to claim 7, wherein the processor displays at least the location of a distal end portion of at least one transseptal apparatus in relation to the fossa ovalis.

11. A non-transitory computer-readable medium according to claim 10, further comprising instructions to transmit the location of at least the distal end portion of the at least one transseptal apparatus by one of: an audible indication, a tactile indication, and a visual indication.

12. A method of locating the fossa ovalis in a patient, performed by a clinician or a central processing unit-controlled surgical system, comprising:
   locating the coronary sinus ostium; and
   locating the plane of the interatrial septum; and
   determining the location of the fossa ovalis on the basis of one or more of the location of the coronary sinus ostium and the location of the plane of the interatrial septum.

13. A method according to claim 12, wherein said locating steps are performed using an electroanatomical navigation system which includes a display screen configured for displaying the three-dimensional location of one or more catheters positioned within a patient's heart.

14. A method according to claim 13, further comprising the step of performing a transseptal puncture after said step of locating the fossa ovalis.

15. A method according to claim 13, wherein the location of the fossa ovalis comprises an area approximately in the plane of the interatrial septum wherein the anterior and posterior limits of the defined area are predetermined distances from the coronary sinus ostium.

16. A method according to claim 15, wherein said electroanatomical navigation system stores said distances in the electroanatomical navigation system and defines and displays the location of the fossa ovalis.

17. A method according to claim 16, wherein said electroanatomical navigation system comprises a display screen with a visual representation of the location of the fossa ovalis.

18. A method according to claim 17, wherein said visual representation comprises an indication of a probability for locating the fossa ovalis at a point.

19. A method according to claim 18, wherein said indication comprises at least one of: an audible indication, a tactile indication, and a visual indication.

20. A method according to claim 19, wherein said indication comprises at least one of: a density of dots, a color, a flashing icon, a clarity of display, a brightness of the visual indication, and a color.

* * * * *